(12) United States Patent
Sacks et al.

(10) Patent No.: US 7,947,304 B2
(45) Date of Patent: May 24, 2011

(54) HUMAN GROWTH HORMONE PATCH FORMULATIONS

(75) Inventors: Hagit Sacks, Modi'in (IL); Meir Stern, Rehovot (IL)

(73) Assignee: TransPharma Medical Ltd., Lod (IL)

( * ) Notice: Subject to any disclaimer, the term of this patent is extended or adjusted under 35 U.S.C. 154(b) by 0 days.

(21) Appl. No.: 12/092,239

(22) PCT Filed: Nov. 2, 2006

(86) PCT No.: PCT/US2006/042894
§ 371 (c)(1), (2), (4) Date: Apr. 30, 2008

(87) PCT Pub. No.: WO2007/056105
PCT Pub. Date: May 18, 2007

(65) Prior Publication Data
US 2008/0226703 A1 Sep. 18, 2008

Related U.S. Application Data

(60) Provisional application No. 60/733,005, filed on Nov. 2, 2005, provisional application No. 60/739,288, filed on Nov. 22, 2005.

(51) Int. Cl.
*A61K 39/00* (2006.01)
*A61K 38/27* (2006.01)
*A61F 13/00* (2006.01)
(52) U.S. Cl. .................... 424/449; 514/11.4; 424/198.1
(58) Field of Classification Search .................... None
See application file for complete search history.

(56) References Cited

U.S. PATENT DOCUMENTS

| | | | |
|---|---|---|---|
| 5,008,110 A | 4/1991 | Benecke et al. | 424/448 |
| 5,096,885 A | 3/1992 | Pearlman et al. | 514/12 |
| 5,567,677 A | 10/1996 | Castensson et al. | 514/12 |
| 5,750,138 A | 5/1998 | Saaman et al. | 424/448 |
| 5,763,215 A | 6/1998 | Blumberg et al. | 435/69.1 |
| 5,948,433 A | 9/1999 | Burton et al. | 424/448 |
| 5,985,311 A | 11/1999 | Cordes et al. | 424/428 |
| 6,689,789 B2 | 2/2004 | Cooper et al. | 514/290 |
| 6,708,060 B1 | 3/2004 | Avrahami et al. | 604/20 |
| 7,387,788 B1 * | 6/2008 | Carrara et al. | 424/449 |
| 2004/0137044 A1 | 7/2004 | Stern et al. | 424/447 |
| 2006/0252682 A1 | 11/2006 | Donati et al. | 514/12 |

FOREIGN PATENT DOCUMENTS

| | | |
|---|---|---|
| WO | WO 93/19776 | 10/1993 |
| WO | WO 2004/039428 A2 | 5/2004 |
| WO | WO 2004/082707 A2 | 9/2004 |
| WO | WO 2006/131931 | 12/2006 |

OTHER PUBLICATIONS

International Search Report of PCT/US2006/42894, dated May 11, 2007.
International Search Report PCT/US2006/042894, Jul. 5, 2007.
Henzl MR. et al., "Optimizing delivery of therapeutics: percutaneous technologies". Bratisl Lek Listy. 2002; 103(4-5):144-51.

* cited by examiner

*Primary Examiner* — Elly-Gerald Stoica
(74) *Attorney, Agent, or Firm* — Winston & Strawn LLP

(57) ABSTRACT

The invention encompasses a transdermal patch formulation comprising hGH, at least one sugar, one amino acid or polyol, and a buffer, wherein the buffer maintains the pH of the formulation in the range of about 5 to about 9 and the formulation does not contain both glycine and mannitol.

10 Claims, 1 Drawing Sheet

Figure 1: Comparison of pig Plasma Levels of hGH when Administered by Injection and Patches
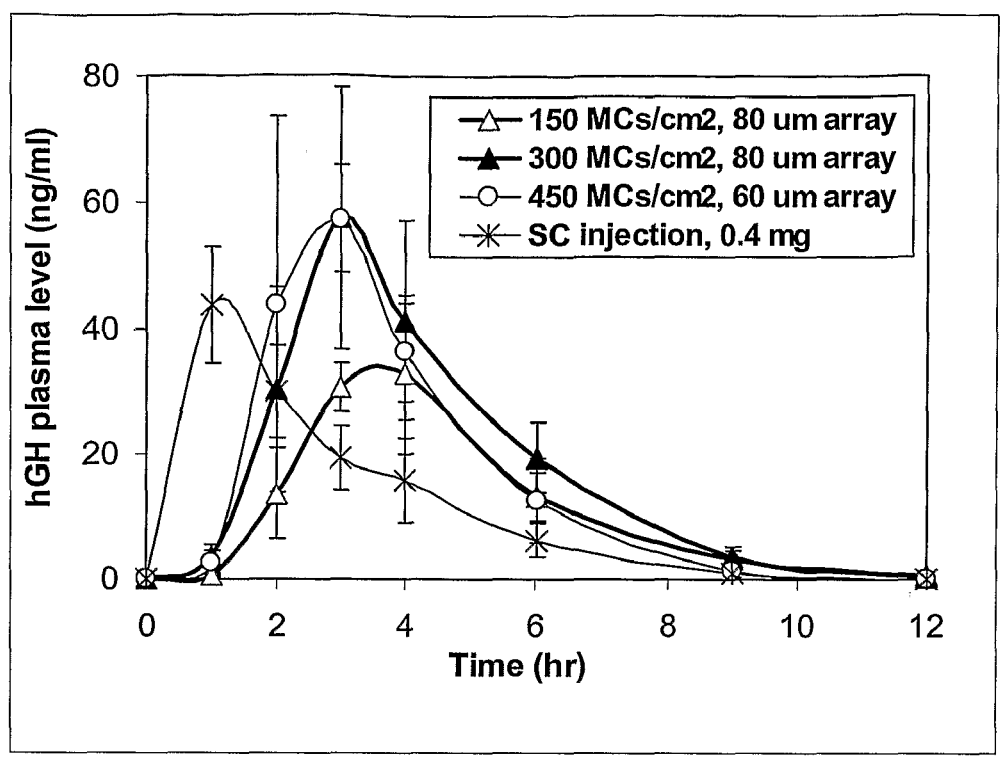

HUMAN GROWTH HORMONE PATCH FORMULATIONS

RELATED APPLICATIONS

This application claims the benefit of U.S. provisional Application Ser. Nos. 60/733,005, filed Nov. 2, 2005 and 60/739,288, filed Nov. 22, 2005, hereby incorporated by reference.

FIELD OF THE INVENTION

This invention encompasses human growth hormone formulations for use in transdermal patches and methods of their preparation.

BACKGROUND OF THE INVENTION

Human growth hormone ("hGH") is a hormone secreted by the human pituitary glands. It consists of 191 amino acids and has a molecular weight of about 22,000. hGH is commonly administered to person with a deficiency of this hormone in order to promote growth of organ systems, such as the skeleton, connective tissue, muscles, liver, intestines, and kidneys.

hGH has been formulated for pharmaceutical administration through subcutaneous injection. See U.S. Pat. No. 5,096,885. These hGH formulations have generally included various excipients such as sugars, surfactants, preservatives, and salts. However, subcutaneous injection is frequently associated with pain and poor compliance. Therefore, an alternative delivery method that eliminates such disadvantages is desirable.

The transdermal patch offers a painless, more convenient, needle-free platform as an alternative to subcutaneous injections. The present invention encompasses formulations of hGH for administration using transdermal patches as well as methods of preparation of those formulations of hGH.

SUMMARY OF THE INVENTION

One embodiment of the invention encompasses a transdermal patch formulation comprising hGH, at least one sugar, one amino acid or polyol, and a buffer, wherein the buffer maintains the pH of the formulation in the range of about 5 to about 9 and the formulation does not contain both glycine and mannitol. Typically, the hGH may be present in an amount sufficient to achieve a formulation concentration of about 10 mg/ml to 255 mg/ml and preferably, the hGH concentration of the formulation may be from about 20 mg/ml to about 170 mg/ml.

In the transdermal patch formulation, the sugar may be glucose, fructose, sucrose, or trehalose and preferably, the sugar may be sucrose or trehalose. Typically, the sugar may be present in an amount sufficient to achieve a formulation concentration of about 11 mg/ml to 300 mg/ml, and preferably, the sugar is present in an amount sufficient to achieve a formulation concentration of about 22 mg/ml to about 200 mg/ml.

In the transdermal patch formulation, the polyol may be mannitol or glycerin. The polyol may be present in the formulation in an amount sufficient to achieve a formulation concentration of about 5 mg/ml to 150 mg/ml and preferably, polyol may be present in an amount sufficient to achieve a formulation concentration of about 10 mg/ml to about 100 mg/ml.

In the transdermal patch formulation, the amino acid may be glycine. The amino acid may be present in an amount sufficient to achieve a formulation concentration of about 3 mg/ml to about 99 mg/ml and preferably in an amount sufficient to achieve a formulation concentration of about 6 mg/ml to about 66 mg/ml.

In the transdermal patch formulation, the buffer may be a phosphate buffer or a citrate buffer. The buffer may be present in an amount sufficient to achieve a formulation pH of about 6 to 8.

Another embodiment of the invention encompasses a transdermal patch formulation comprising hGH, sucrose, and glycine in a 30 mM phosphate buffer, wherein the concentration ratio (mg/ml) of hGH, sucrose, and glycine is about 85:100:33 to about 100:120:40. Typically, the pH of transdermal patch formulation is from about 6 to about 8.

Yet another embodiment of the invention encompasses a transdermal patch formulation comprising hGH, trehalose, and mannitol dissolved in a 20 mM citrate buffer, wherein the concentration ratio (mg/ml) of hGH, trehalose, and mannitol is about 85:100:50 to about 100:120:60 and the pH is from about 6 to 8.

One embodiment of the invention encompasses methods for preparing a transdermal formulation of hGH comprising dissolving at least one sugar and at least one polyol or amino acid in a buffer to form an excipient solution; dissolving hGH in the excipient solution to obtain a hGH formulation having a hGH concentration of about 10 mg/ml to 255 mg/ml; and storing the hGH formulation for a time sufficient to promote dissolution, wherein the formulation has a pH of about 6 to 8. Optionally, the method may further comprise removing any non-dissolved particles of hGH after storage.

Another embodiment of the invention encompasses a method for preparing a transdermal formulation of hGH comprising forming an excipient solution by dissolving sucrose and glycine in 30 mM phosphate buffer to achieve a formulation concentration of about 100 mg/ml of sucrose and about 33 mg/ml of glycine and a final formulation pH of about 7.5±0.5; dissolving hGH in the excipient solution to achieve a hGH final concentration of about 85-100 mg/ml; storing the hGH solution to promote dissolution; and optionally, removing any non-dissolved particles of hGH.

Yet another embodiment of the invention encompasses a transdermal patch comprising a formulation of hGH, at least one sugar, at least one polyol, and a buffer in an amount sufficient to maintain the formulation pH in the range of about 6 to about 8, wherein after six months of storage at a temperature of about 4° C., the patch has related hGH proteins in an amount of about 0.5% to about 13% and aggregate proteins in an amount of about 0.01% to about 6% by weight and the formulation does not contain both glycine and mannitol. Preferably, after storage for six months at a temperature of about 4° C., the transdermal patch formulation has related proteins in an amount of about 2% to 10% by weight. Preferably, after storage for six months at a temperature of about 4° C., the transdermal patch has aggregate proteins in an amount of about 0.2% to 4% by weight.

BRIEF DESCRIPTION OF THE FIGURES

FIG. 1 illustrates the drug delivery profile of transdermal patches in pigs using the formulation of the invention as compared to an injectable dosage form.

DETAILED DESCRIPTION OF THE INVENTION

The invention encompasses hGH formulations for use in transdermal patches, as well as methods of their preparation.

Because the formulations are designed for use with patch manufacturing, the hGH formulations are prepared in a concentrated solution of hGH, such that when administered to a patient in the form of a patch, the formulations of the invention achieve a pharmacokinetic profile sufficient to achieve the desired result.

The formulations of the invention comprise hGH, at least one sugar, at least one polyol or amino acid, and a buffer, wherein the buffer maintains the pH of the formulation in the range of about 6 to about 8 and the formulation does not contain both glycine and mannitol.

The hGH used in the formulations is readily available from commercial sources. For example, the hGH can be obtained from Bio-Technology General Ltd. (Israel) or BresaGen Ltd. (Australia). hGH can also be obtained as described in U.S. Pat. No. 5,763,215. As used herein, the term "hGH" or "human growth hormone" also includes biologically active human growth hormone equivalents; e.g., differing in one or more amino acid(s) in the overall sequence as well as Met-hGH (192 amino acids). Further, the terms as used are intended to cover substitution, deletion, and insertion amino acid variants of hGH, or post translational modifications. Typically, the hGH is present in the formulation in an amount sufficient to achieve a formulation concentration of about 10 mg/ml to 255 mg/ml. Preferably, the hGH concentration of the formulation is from about 20 mg/ml to about 170 mg/ml, and more preferably, the hGH concentration of the formulation is about 30 mg/ml to about 120 mg/ml.

The sugar may be any pharmaceutically acceptable sugar. Sugars include, but are not limited to, monosaccharides, disaccharides, and polysaccharides. Preferred sugars include glucose, fructose, sucrose, trehalose, lactose, maltose, galactose, sorbitol, or xylitol. Preferably, the sugar is sucrose or trehalose. Typically, the sugar is present in the formulation in an amount sufficient to achieve a formulation concentration of about 11 mg/ml to 300 mg/ml. Preferably, the sugar concentration of the formulation is about 22 mg/ml to about 200 mg/ml, and more preferably, the sugar concentration of the formulation is about 30 mg/ml to about 120 mg/ml.

The polyol may be any pharmaceutically acceptable polyol. Polyols include, but are not limited to, mannitol, glycerin, polyethylene glycol, or block copolymers such as α-hydro-omega-hydroxypoly(oxyethylene)poly(oxypropylene)poly(oxyethylene) block copolymer. Preferably, the polyols include mannitol. Typically, the polyol is present in the formulation in an amount sufficient to achieve a formulation concentration of about 5 mg/ml to 150 mg/ml. Preferably, the polyol concentration of the formulation is about 10 mg/ml to about 100 mg/ml, and more preferably, the polyol concentration of the formulation is about 15 mg/ml to about 70 mg/ml.

The amino acid may be any pharmaceutically acceptable amino acid. Amino acids include, but are not limited to, glycine or histidine. A preferred amino acid is glycine. Typically, the amino acid in the formulation is present in an amount sufficient to achieve a formulation concentration of about 3 mg/ml to about 99 mg/ml. Preferably, the amino acid formulation concentration is about 6 mg/ml to 66 mg/ml, and more preferably, the amino acid formulation concentration is about 10 mg/ml to 50 mg/ml.

The buffer may be any buffer that maintains the desired pH and is physiologically compatible. One of ordinary skill in the art with little or no experimentation can easily determine the type and amount of buffer necessary to achieve the desired pH. Preferably, the buffer is a phosphate buffer, a citrate buffer, phosphate-acetate buffer, citrate-phosphate buffer, or succinate buffer. The buffer should be present in an amount sufficient to achieve a formulation pH of about 5 to 9, preferably of about 6 to 8, and more preferably of about 6.5 to 7.5.

In one preferred embodiment, the formulation comprises hGH, sucrose, and glycine in a 30 mM phosphate buffer, herein defined as hGH Formulation I. In hGH Formulation I, the concentration ratio (mg/ml) of hGH, sucrose, and glycine is about 0.85:0.80:0.26 to about 0.85:1.20:0.40, respectively, and preferably 0.85:1.00:0.33. The pH of hGH Formulation I is from about 6 to about 8.

In another preferred embodiment, the formulation comprises hGH, trehalose, and mannitol dissolved in a 20 mM citrate buffer, herein defined as hGH Formulation II. In hGH Formulation II, the concentration ratio (mg/ml) of hGH, trehalose, and mannitol is about 0.85:0.8:0.4 to about 0.85:1.20:0.60, respectively, and preferably, 0.85:1.00:0.50, respectively. The pH of hGH Formulation II is from about 6 to 8.

The invention encompasses methods of preparing the formulation. The method for preparing a transdermal formulation of hGH comprises dissolving at least one sugar and at least one polyol or amino acid in a buffer to form an excipient solution; dissolving hGH in the excipient solution to obtain a hGH formulation having a hGH concentration of about 10 mg/ml to 255 mg/ml; and storing the hGH formulation for a time sufficient to promote dissolution, wherein the formulation has a pH of about 6 to 8 and the formulation does not contain both glycine and mannitol. Optionally, the method may further comprise removing non-dissolved particles of hGH. Typically, the hGH, sugar, polyol, amino acid, and buffer are added in amounts sufficient to achieve the concentrations disclosed above for the hGH formulations.

Using methods commonly known to the skilled artisan, the artisan can easily determine with little or no experimentation the methods necessary for dissolving, mixing, storing, the formulation and if necessary of removing non-dissolved particles of hGH.

One preferred method of preparing hGH Formulation I comprises dissolving sucrose and glycine in 30 mM phosphate buffer to achieve a final concentration of about 100 mg/ml of sucrose and about 33 mg/ml of glycine and a final formulation pH of about 7.5±0.5. The hGH is then dissolved in the solution to achieve a final concentration of about 85-100 mg/ml. The formulated hGH solution is stored to promote dissolution. Preferably, the solution is stored overnight at a temperature of 5±3° C. Thereafter, the non-dissolved particles are removed from the solution by any means known to the skilled artisan. Preferably, the non-dissolved particles are removed by filtration or centrifugation.

One preferred method of preparing hGH Formulation II comprises dissolving trehalose and mannitol in 20 mM citrate buffer to achieve final concentrations of about 100 mg/ml of trehalose and about 50 mg/ml of mannitol and a final formulation pH of about 6.7±0.5. The hGH is then dissolved in the solution to achieve a final concentration of about 85-100 mg/ml. The formulated hGH solution is stored to promote dissolution. Preferably, the formulation is stored overnight at 5±3° C. Thereafter, the non-dissolved particles are removed from the solution by any means known to the skilled artisan. Preferably, the non-dissolved particles are removed by filtration or centrifugation.

Yet another embodiment of the invention encompasses transdermal patches and methods of making the transdermal patches having the formulation of the invention.

Typically, a transdermal patch comprises a formulation of hGH, at least one sugar, at least one polyol or glycine, and a buffer in an amount sufficient to maintain the formulation pH in the range of about 6 to about 8, wherein after six months of storage at a temperature of about 4° C. to about room temperature, the patch has related hGH proteins in an amount of about 4% to about 13% and aggregate proteins in an amount of about 0.1% to about 6% by weight. As used herein, the term "aggregate proteins" refers to adducts of at least two molecules forming a dimer and adducts of other impurities of higher molecular weight. As used herein, unless otherwise define the term "related proteins" refers to deamidated forms, oxidation forms, and other impurities such as translocated, cleaved, and truncated proteins.

Preferably, after storage for six months at a temperature of about 4° C., the transdermal patch has related proteins in an amount of about 0.5% to 13% by weight and more preferably, in an amount of about 2% to 10%. Preferably, after storage for six months at a temperature of about 4° C. the transdermal patch has aggregate proteins in an amount of about 0.01% to 6% by weight and more preferably, in an amount of about 0.2% to 4%.

The formulations of the invention may be used to prepare patches having various doses of hGH. Printing and patch technology is generally described in U.S. Pat. Nos. 6,689,789; 5,985,311; 5,948,433; 5,750,138; and 5,008,110, hereby incorporated by reference. Preferably, the patches are prepared using the printing and patch production technology disclosed in U.S. Publication No. 2004/137,044, hereby incorporated by reference. The dose density of hGH on the patch is from 0.01-1.6 mg hGH per cm².

In one embodiment, the hGH formulations of the invention are administered using the Viaderm device, which uses radiofrequency to induce microchannels in the skin. The device is described inter alia, in U.S. Pat. No. 6,708,060. Following creation of the microchannels, the patch containing the drug formulation is applied to the skin.

The stability of the patches is typically studied to determine storage conditions and shelf life. The appearance, identity, purity, and quantity, along with other tests can be studied for each patch. All patches should meet the specifications according to the European Pharmacopeia guidelines for hGH (EP 5.0 (2005)) or US guidelines (USP 28 (2005)). The formulations of the invention have been shown to be particularly stable when printed on the patch, and achieve PK profiles similar to subcutaneous injection in pigs. The use of commercial formulations of hGH is limited with respect to the dose that can be printed on the patch and therefore will not result in sufficient levels of hGH in the blood.

The invention is further defined by reference to the following non-limiting examples describing in detail the formulations and methods described above. It will be apparent to one skilled in the art that many modifications, both to materials and methods, may be practiced without departing from the scope of the invention.

EXAMPLES

Example 1

Preparation of hGH Formulation I

An excipient solution of phosphate buffer containing sucrose and glycine was prepared by dissolving sucrose and glycine in 30 mM phosphate buffer, pH 6, such that final concentrations of 100 mg/ml of sucrose and 33 mg/ml of glycine were achieved. hGH was then dissolved in the excipient solution at a concentration of 85 mg/ml. The formulated hGH solution was left standing overnight at 5±3° C. to promote dissolution. The non-dissolved particles were then removed by two cycles of centrifugation for 5 minutes at 3940 g. The final concentration of the formulation's components was 85:100:33 mg/ml for hGH, sucrose, and glycine, respectively. The final formulation pH was 7.5±0.5.

Example 2

Preparation of hGH Formulation II

An excipient solution of citrate buffer containing trehalose and mannitol was prepared by dissolving trehalose and mannitol in 20 mM citrate buffer, pH 4, such that final concentrations of 85 mg/ml of trehalose and 50 mg/ml of mannitol were achieved. hGH was then dissolved in the excipient solution at a concentration of 85 mg/ml. The formulated hGH solution was left standing overnight at 4° C. to promote dissolution. The non-dissolved particles were then removed by two cycles of centrifugation for 5 minutes at 3940 g. The final concentration of the formulation's components was 85:100:50 mg/ml for hGH, trehalose, and mannitol, respectively. The final formulation pH was 6.7±0.5.

Example 3

Preparation of Test Patches

Test patches were prepared with hGH Formulations I and II. The test patches were manufactured using the printing and patch production technology disclosed in U.S. Publication No. 2004/0137044 and BLF2080 printing liner (Dow). Test patches were manufactured using the MAXNC equipment at sizes of 1.4 cm² and dose of 1 mg (parallel to 4 mg per 5 cm² patch). Each printed patch was individually packed in a histosette frame. Each histosette containing the printed core was packed in a sealed laminated aluminum bag with silica gel and argon.

Example 4

Preparation of Verification Patches

Verification patches were prepared from various doses of hGH Formulations I and II. The verification patches were manufactured using the printing and patch production technology disclosed in U.S. Publication No. 2004/0137044 and BLF2080 (Dow) printing liner. The verification patches were manufactured using the BioDot AD 3200 equipment at sizes of 5 cm² and doses of 2 and 6 mg. The patch structure design described in PCT application No. PCT/IL2006/000679, which claims the benefit of U.S. provisional No. 60/689,763, was utilized. The patch component included the following transdermal liners: 3M-9733 foam tape, 3M-9877 double coated medical tape, 3M-9907W backing Nonwoven tape, and 3M-Scotchpak 9742 release liner. Each patch was individually packed and sealed in a laminated aluminum bag with silica gel and argon.

Example 5

Stability of the Formulations

TABLE 1

Summary of stability specification of hGH printed patch

| Tests | analytical procedure | Acceptance Limits |
|---|---|---|
| APPEARANCE | | |
| State | Visual inspection | The drug liner is Transparent backing liner with clear or white dots |
| IDENTITY | | |
| Distribution of polyacrylamide gel according to isoelectric point | Isoelectric focusing | In the electropherogram obtained with test solution (30 mcg of protein) the principal band corresponds in position to that in the electropherogram obtained with reference solution (30 mcg of protein) |
| Distribution in chromatographic column according to protein hydrophobic properties | RP-HPLC | The retention time of the principal peak in the chromatogram obtained with the test solution is similar to that of the principal peak in the chromatogram obtained with the reference solution |
| Distribution in chromatographic column according to protein molecular size | SE-HPLC | The retention time of the principal peak in the chromatogram obtained with the test solution is similar to that of the principal peak in the chromatogram obtained with the reference solution |
| PURITY | | |
| Related proteins | RP-HPLC | In the chromatogram obtained with the test solution the sum of the areas of all peaks, apart from the principal peak, is not greater than 13 percent of the total area of the peaks |
| Dimer and related substances of higher molecular mass | SE-HPLC | In the chromatogram obtained with the test solution the sum of the areas of all peaks with a retention time less than that of the principal peak is not greater than 6.0 percent of the total area of the peaks |
| Isoform distribution | Isoelectric focusing | The electropherogram obtained with reference solution (30 mcg of protein) contains a major band with an isoelectric point of approximately five and a slightly more acidic minor band at approximately 4.8 In the electropherogram obtained with test solution (30 mcg of protein) no band apart from the major band is more intense than the major band in the electropherogram obtained with test solution (1.88 mcg of protein, i.e. 6.25 percent) |
| QUANTITY | | |
| hGH monomer amount | SE-HPLC | 90.0-110.0 percent of label claim |
| OTHER TESTS | | |
| Uniformity of dosage content | SE-HPLC | The amount of protein in each of the patches is 90.0-110.0 percent of label claim measured with relative standard deviation not higher than 6.0 percent (N = 10) |
| Water Content | KF | N/A (For information only) |
| Biological activity | cell proliferation test | N/A (For information only) |
| Drug release (dissolution) | | N/A (For information only) |
| Total aerobic count | | NMT 100 CFU/patch |
| Total anaerobic count | | Non detected |
| Bacterial Endotoxin | | LT 5 EU/patch |

The stability of patches made with hGH Formulations I and II was measured upon storage for 1, 2, 3, and 6 months at room temperature and upon storage for 3 and 6 months at 5±3° C. The patches contained 1 mg hGH per patch on a 1.4 cm² patch. Stability tests were performed in triplicate. The results of the stability tests are contained in Table 2. The test patches conformed to all appearance and identity tests. In Tables 2, 3a, and 3b, the following definitions were used RT="room temperature;" NP="not performed", LT="less than;" NMT="not more than;" and ND="not determined."

TABLE 2

Stability of Test Patches

| Formulation | Storage Conditions Temperature | Time (mos.) | Purity Related Proteins (NMT 13%) | Aggregates (NMT 6.0%) | Isoform distribution | Quantity Patch Assay (90 ÷ 110%) | Other Tests Water Content (μg/patch) | (% w/w) | Drug Release (% of total recovered) |
|---|---|---|---|---|---|---|---|---|---|
| I | RT | 0 | 3 | 0.6 | Conform | 101.2 | NP | NP | 73.7 ± 2.5 |
|   | RT | 1 | 5 | 0.6 |  | 101.4 | 47 | 2.0 | 80.9 ± 1.8 |
|   | RT | 2 | 7 | 0.8 |  | 100.9 | 39 | 1.6 | 83.4 ± 1.5 |
|   | RT | 3 | 5 | 0.7 |  | 101.5 | 58 | 2.4 | 88.7 ± 1.4 |
|   | 4° C. | 3 | 4 | 0.7 |  | 102.3 | 80 | 3.3 | 81.3 ± 1.3 |
|   | RT | 6 | 8 | 0.7 |  | 98.1 | 60 | 2.6 | 79.7 ± 5.0 |
|   | 4° C. | 6 | 7 | 0.4 |  | 96.1 | 90 | 3.8 | 85.2 ± 2.7 |
| II | RT | 0 | 4 | LT 0.4 | Conform | 9.3 | 67 | 2.6 | 89.7 ± 2.0 |
|   | RT | 1 | 4 | 0.6 |  | 99.5 | 51 | 2.0 | 86.5 ± 0.9 |
|   | RT | 2 | 3 | 0.6 |  | 100.5 | 53 | 2.1 | 92.1 ± 0.5 |
|   | RT | 3 | 4 | 0.6 |  | 97.9 | 41 | 1.6 | 91.8 ± 0.4 |
|   | 4° C. | 3 | 4 | 0.5 |  | 98.3 | 104 | 4.0 | 89.9 ± 0.8 |
|   | RT | 6 | 10 | 1.0 |  | 96.7 | 39 | 1.6 | 86.7 ± 1.9 |
|   | 4° C. | 6 | 8 | 0.6 |  | 95.7 | 67 | 2.7 | 95.2 ± 2.4 |

The stability of the verification patches made from hGH Formulations I and II was measured upon storage for 1, 2, and 3 months at room temperature and upon storage for 3 months at 5±3° C. The verification patches contained 2 and 6 mg hGH per patch on a 5.0 cm² patch. Stability tests were performed in five replicates. The results of the stability tests are contained in Tables 3a and 3b. The verification patches conformed to all appearance, purity, and identity tests.

TABLE 3a

Stability of Verification Patches

| Formulation/ Dose | Storage Conditions Temperature | Time (mos.) | Purity Related Proteins (NMT 13%) | Aggregates (NMT 6.0%) | Isoform distribution | Quantity Patch Assay (90 ÷ 110%) | Other Tests Water Content (μg/patch) | (% w/w) | Drug Release (% of total recovered) |
|---|---|---|---|---|---|---|---|---|---|
| I/2 mg | RT | 0 | 2.7 | 0.8 | Conform | 103.0 | 130.5 | 2.7 | 89.1 ± 3.7 |
|   | RT | 1 | 3.3 | 0.8 |  | 103.6 | 93.7 | 2.0 | 90.6 ± 4.8 |
|   | RT | 2 | 3.9 | 0.8 |  | 101.8 | 115.9 | 2.4 | 95.3 ± 1.1 |
| I/6 mg | RT | 0 | 3.6 | 0.8 | Conform | 103.5 | 482.1 | 3.3 | 73.6 ± 3.3 |
|   | RT | 1 | 3.5 | 0.9 |  | 101.6 | 396.4 | 2.8 | 78.3 ± 0.6 |
|   | RT | 2 | 3.9 | 0.8 |  | 99.3 | 253.0 | 1.8 | 94.4 ± 2.6 |
| II/2 mg | RT | 0 | 3.1 | 0.7 | Conform | 93.2 | 156.0 | 3.0 | 86.0 ± 1.1 |
|   | RT | 1 | 3.0 | 0.7 |  | 93.1 | 88.4 | 1.7 | 82.2 ± 0.9 |
|   | RT | 2 | 3.4 | 0.7 |  | 91.5 | 30.9 | 0.6 | 89.5 ± 1.3 |
| II/6 mg | RT | 0 | 3.3 | 0.7 | Conform | 104.7 | 604.9 | 3.9 | 77.8 ± 3.1 |
|   | RT | 1 | 3.0 | 0.8 |  | 105.0 | 120.6 | 0.8 | 80.9 ± 0.8 |
|   | RT | 2 | 3.5 | 0.8 |  | 104.7 | 229.0 | 1.5 | 103.8 ± 3.0 |

TABLE 3b

Stability of Verification Patches (continued)

| Formulation/Dose | Storage Conditions | | Other Tests | | | |
| --- | --- | --- | --- | --- | --- | --- |
| | Temperature | Time (mos.) | Uniformity of Content | Biological Activity (% of label claim) | Bioburden (CFU/patch) | Bacterial Endotoxin (EU/patch) |
| I/2 mg | RT | 0 | Conform, RSD 0.3 | 50 | 55 (35-81) | 0.34-0.81 |
| | RT | 1 | NP | NP | NP | NP |
| | RT | 2 | NP | 102 | 14 (4-27) | NP |
| I/6 mg | RT | 0 | Conform, RSD 0.6 | 110 | 16 (8-26) | 0.94-1.52 |
| | RT | 1 | NP | NP | NP | NP |
| | RT | 2 | NP | NP | 7 (1-16) | NP |
| II/2 mg | RT | 0 | Conform, RSD 0.5 | 120 | 36 (14-73) | 0.27-0.30 |
| | RT | 1 | NP | NP | NP | NP |
| | RT | 2 | NP | NP | 8 (4-15) | NP |
| II/6 mg | RT | 0 | Conform, RSD 0.3 | 111 | 41 (11-67) | 0.54-0.74 |
| | RT | 1 | NP | NP | NP | NP |
| | RT | 2 | NP | NP | 16 (3-39) | NP |

As illustrated by Tables 2, 3a, and 3b, both test and verification patches made using the formulations of the invention, (hGH Formulations I and II) maintained good stability. The test batches were stable for a minimum of 6 months at both room temperature and 5±3° C. The results of purity tests for both the test and verification patches meet the acceptance limits in Table 1. In addition, biological activity tests of the verification patches made with hGH Formulations I and II at 0 months demonstrated good potency of the printed protein (about 100% of the label claim).

Pharmacokinetic properties in pigs of patches made from hGH Formulation I at a dosage of 4 mg of hGH on a 5.0 cm$^2$ patch were compared to those of 0.4 mg subcutaneous hGH injections. The pharmacokinetic properties of interest include area under the curve ("AUC") and bioavailability. The microchannels per cm$^2$ and the dimension of the electrode arrays were varied with respect to the patches.

Example 6

Pharmacokinetic Study in Pigs

The pharmacokinetic studies were carried out on 10-15 kg white male pigs using the following procedure: The skin application site of the pigs was treated with saline for 30 minutes in order to moisten the site and increase the number of micro-channels in the pigs (about 70%) to the observed percentage in humans (>90%). ViaDerm was then applied using positive feedback setting. The device was applied on the dorsal back area near the spine and was covered with a patch. The pigs were under general anesthesia for the initial procedure, cannulation and 1 hour post patch application, and conscious for the remainder of the trial. Blood was drawn from the jugular cannula into a plasma tube at regular intervals after the administration of the patch. The patch was removed after 12 hours. Analysis of hGH plasma levels was performed by ELISA DSL 10-1900 test. A subcutaneous injection of 0.4 mg hGH (Genotropin, Pharmacia) was used as positive control group for bioavailability calculations.

hGH plasma levels of the patches and injection are reported in FIG. 1. AUC and bioavailability parameters patches made with hGH Formulation I and injection are reported in Table 4. Patches with 150, 300, and 450 microchannels ("MCs") per cm$^2$ and 60-80 µm diameter electrode arrays were compared to a subcutaneous injection ("SC") of 0.4 mg hGH (Genotropin, Pharmacia).

TABLE 4

AUC and Bioavailability Parameters in pigs for hGH when Administered by Injection and Patches

| Treatment | AUC (ng*hr/ml) | Relative Bioavailability (%) |
| --- | --- | --- |
| SC - 0.4 mg | 135 ± 22 | 100 ± 0 |
| 4 mg/patch 150 MCs/cm$^2$ - 80 µm | 137 ± 40 | 10 ± 3 |
| 4 mg/patch 300 MCs/cm$^2$ - 80 µm | 214 ± 57 | 16 ± 4 |
| 4 mg/patch 450 MCs/cm$^2$ - 60 µm | 193 ± 43 | 14 ± 3 |

As illustrated by FIG. 1, the maximum plasma level of hGH is obtained at approximately 1 hour when administered by injection and at approximately 3-4 hours when administered by transdermal patch. With respect to the administration of hGH through the patches, FIG. 1 illustrates that the more microchannels that are used, the higher the transdermal delivery of hGH. Table 4 demonstrates that increasing the dimension of the electrode array has the effect of increasing bioavailability. For example, Table 4 shows that a patch with 300 microchannels/cm$^2$ and an electrode array 80 µm in diameter exhibits similar bioavailability to a patch with 450 microchannels/cm$^2$ and an electrode array 60 µm in diameter (14% vs. 16%).

What is claimed is:

1. A transdermal patch formulation comprising: hGH, wherein the hGH is present in an amount sufficient to achieve a formulation concentration of about 20 mg/ml to 255 mg/ml, sucrose, glycine, and phosphate buffer, wherein the phosphate buffer maintains the pH of the formulation in the range of about 6 to about 8, wherein the hGH, sucrose, and glycine are present in a concentration ratio (mg/ml) of about 0.85:0.80:0.26 to about 0.85:1.20:0.40, and wherein after six months of storage at a temperature of about 4° C. of a transdermal patch comprising the transdermal patch formulation in a dried form, the patch has deamidated, oxidated, cleaved and/or truncated hGH proteins in an amount of about 0.5% to about 13% of hGH and aggregate hGH proteins in an amount of about 0.01% to about 6% of hGH.

2. The transdermal patch formulation according to claim 1, wherein sucrose is present in an amount sufficient to achieve a formulation concentration of about 11 mg/ml to 300 mg/ml.

3. The transdermal patch formulation according to claim 1, wherein glycine is present in the formulation in an amount sufficient to achieve a formulation concentration of about 3 mg/ml to about 99 mg/ml.

4. The transdermal patch formulation according to claim 1, wherein the hGH concentration of the formulation is from about 20 mg/ml to about 170 mg/ml, sucrose is present in an amount sufficient to achieve a formulation concentration of about 22 mg/ml to about 200 mg/ml, glycine is present in the formulation in an amount sufficient to achieve a formulation concentration of about 6 mg/ml to about 66 mg/ml, and phosphate buffer.

5. A transdermal patch formulation of hGH prepared according to a method comprising:
dissolving sucrose and glycine in phosphate buffer to form an excipient solution;
dissolving hGH in the excipient solution to obtain a hGH formulation having a hGH concentration of about 20 mg/ml to 255 mg/ml;
providing the hGH, sucrose and glycine in the formulation at a concentration ratio (mg/ml) of about 0.85:0.80:0.26 to about 0.85:1.20:0.40; and
storing the hGH formulation,
wherein the formulation has a pH of about 6 to 8.

6. The transdermal patch formulation according to claim 5, wherein the method further comprises removing any non-dissolved particles of hGH after storing the hGH formulation.

7. The transdermal patch formulation according to claim 5 wherein the excipient solution is formed by dissolving sucrose and glycine in a 30 mM phosphate buffer to achieve a formulation concentration of about 100 mg/ml of sucrose and about 33 mg/ml of glycine and a final formulation pH of about 7.5+−0.5; the hGH is dissolved in the excipient solution to achieve a hGH final concentration of about 85 mg/ml to 100 mg/ml; and, after storing the hGH formulation, optionally removing any non-dissolved particles of hGH.

8. A transdermal patch comprising a formulation of hGH, wherein the hGH is present in an amount sufficient to achieve a formulation concentration of about 20 mg/ml to 255 mg/ml, sucrose glycine, and phosphate buffer in an amount sufficient to maintain the formulation pH in the range of about 6 to about 8, wherein after six months of storage at a temperature of about 4° C., the patch has deamidated, oxidized, cleaved and/or truncated hGH proteins in an amount of about 0.5% to about 13% of hGH and aggregate hGH proteins in an amount of about 0.01% to about 6% of hGH, and wherein said hGH, sucrose, and glycine are present in a concentration ratio (mg/ml) of about 0.85:0.80:0.26 to about 0.85:1.20:0.40.

9. The transdermal patch according to claim 8, wherein after storage for six months at a temperature of about 4° C., the transdermal patch has deamidated, oxidized, cleaved and/or truncated hGH proteins in an amount of about 2% to 10% of hGH.

10. The transdermal patch according to claim 8, wherein after storage for six months at a temperature of about 4° C., the transdermal patch has aggregate hGH proteins in an amount of about 0.2% to 4% of hGH.

* * * * *

UNITED STATES PATENT AND TRADEMARK OFFICE
CERTIFICATE OF CORRECTION

Page 1 of 1

PATENT NO.         : 7,947,304 B2
APPLICATION NO.    : 12/092239
DATED              : May 24, 2011
INVENTOR(S)        : Sacks et al.

It is certified that error appears in the above-identified patent and that said Letters Patent is hereby corrected as shown below:

Column 1:
Line 6, after "This application" insert -- is a 371 filing of International Patent Application PCT/US2006/042894 filed November 2, 2006, which --.

Column 14:
Line 13 (claim 8, line 4), change "sucrose glycine," to -- sucrose, glycine, --.

Signed and Sealed this
Fifth Day of July, 2011

David J. Kappos
*Director of the United States Patent and Trademark Office*